United States Patent [19]

Kronner

[11] 4,127,119
[45] Nov. 28, 1978

[54] FRACTURE REDUCING AND JOINT IMMOBILIZING APPARATUS

[76] Inventor: Richard F. Kronner, Rte. 2, Box 583, Roseburg, Oreg. 97470

[21] Appl. No.: 794,417

[22] Filed: May 6, 1977

Related U.S. Application Data

[63] Continuation-in-part of Ser. No. 712,842, Aug. 9, 1976, abandoned.

[51] Int. Cl.² ............................................. A61F 5/04
[52] U.S. Cl. .................. 128/92 A; 128/84 B
[58] Field of Search .................. 128/84 R, 84 B, 83, 128/92 R, 92 A, 92 B, 92 E, 87 R

[56] References Cited

U.S. PATENT DOCUMENTS

| | | | |
|---|---|---|---|
| 2,055,024 | 9/1936 | Bittner, Jr. | 128/84 B |
| 2,110,414 | 3/1938 | Bell | 128/84 B |
| 2,238,869 | 4/1941 | Haynes | 128/84 B X |
| 3,976,061 | 8/1976 | Volkov et al. | 128/84 B |
| 3,977,397 | 8/1976 | Kalnberz et al. | 128/92 A |

Primary Examiner—John D. Yasko
Attorney, Agent, or Firm—James D. Givnan, Jr.

[57] ABSTRACT

The apparatus includes upper and lower pin holder assemblies of ring-like configuration which may be opened for application to the limb. Each pin holder assembly includes opposed wall structures within which bone penetrating pins are secured to firmly attach each pin holder assembly to the bone segment. Elongate connector assemblies extend between the upper and lower pin holder assemblies with each of the connector assemblies including spherical coupling components which permit adjustment of the pin holder assemblies in a universal manner. Each connector assembly includes nut elements which dually serve to position an intermediate spherical component along the connector shaft for locked engagement with the ring structure of a pin holder assembly.

10 Claims, 22 Drawing Figures

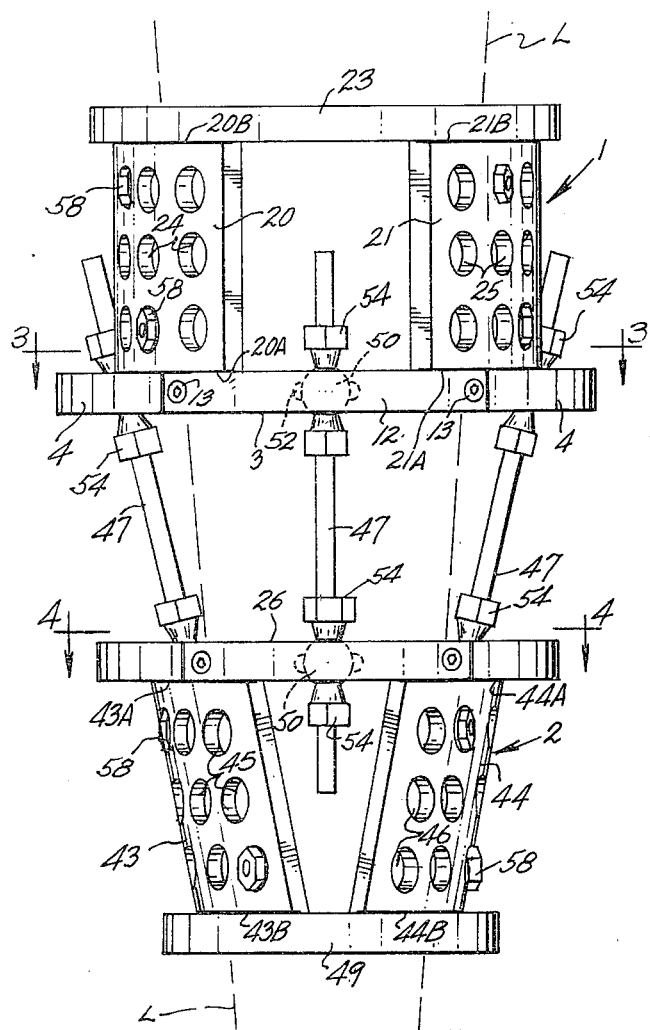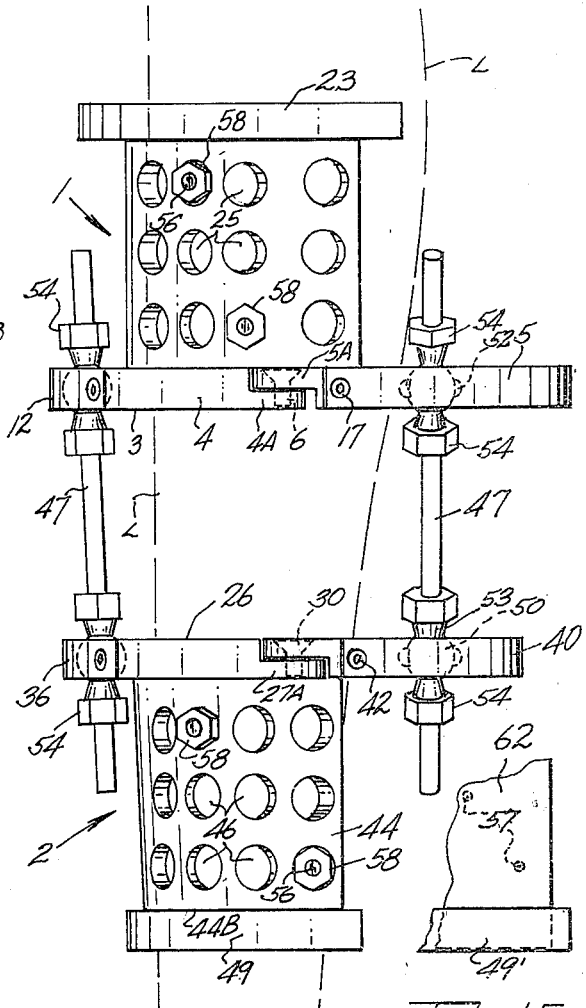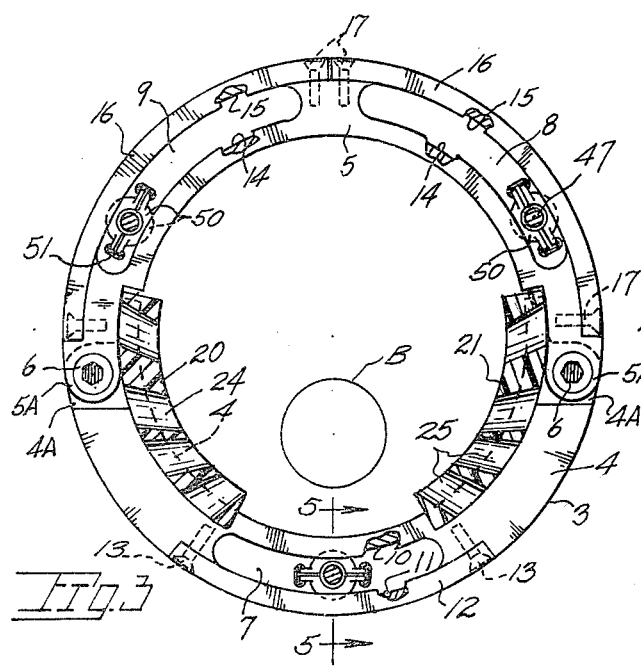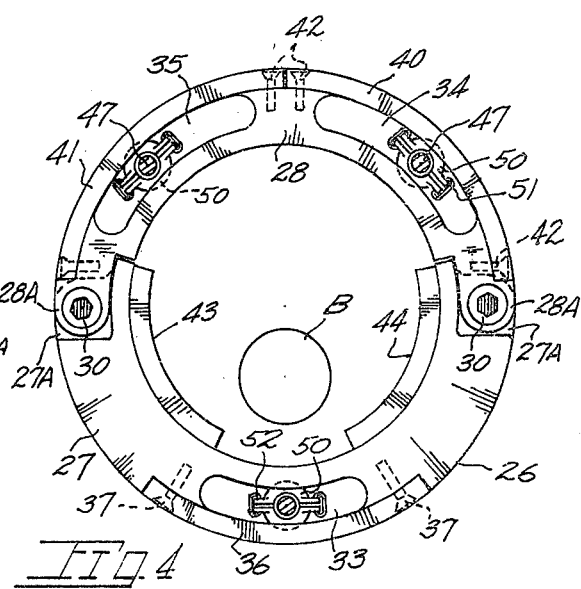

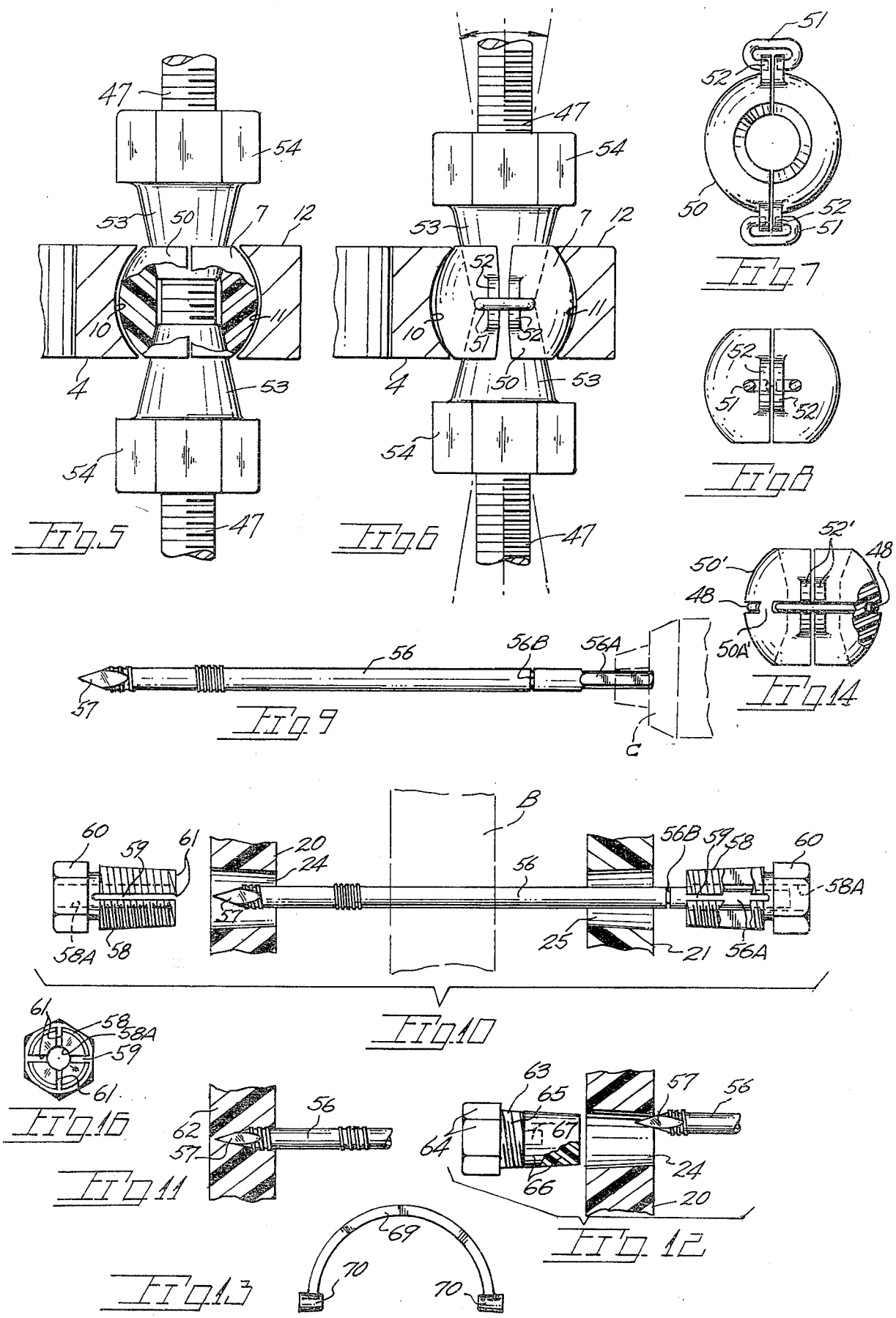

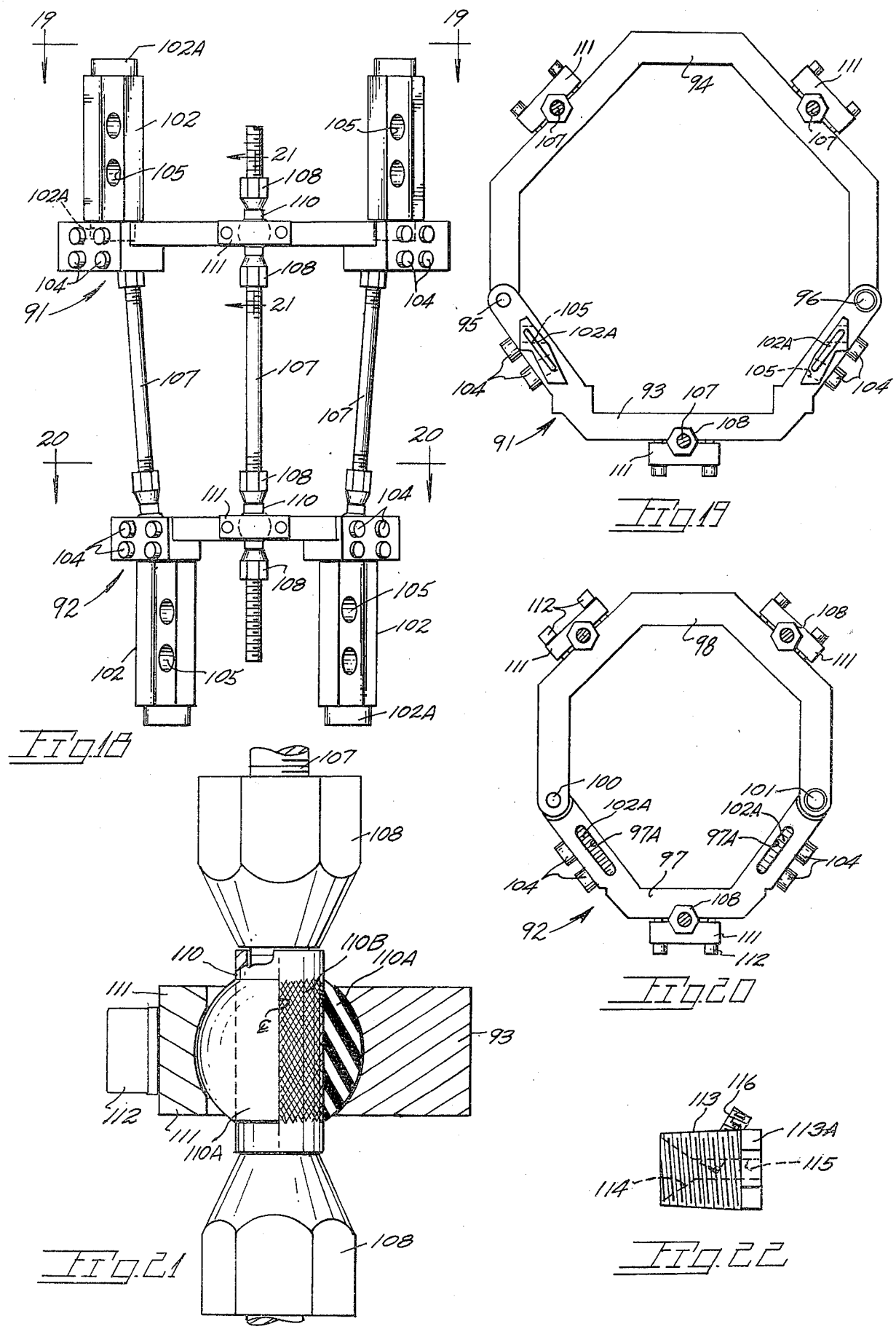

FRACTURE REDUCING AND JOINT IMMOBILIZING APPARATUS

BACKGROUND OF THE INVENTION

The present application is a continuation-in-part of my copending U.S. patent application bearing the same title filed Aug. 9, 1976 under Ser. No. 712,842 now abandoned.

The present invention relates to orthopedic equipment and particularly to an apparatus for application to an arm or leg member with a fractured bone or joint to be immobilized for the purposes of positioning and retention of the bone segments to facilitate the healing process.

The practice of applying traction to a limb is well known as are the attendant inconveniences to the patient. More importantly, the immobile status of the patient in traction engenders further medical complications. Additionally, the several weeks hospital stay in traction is very costly to the patient both from an expense standpoint as well as loss of income from any productive effort.

It has been recognized that numerous advantages reside in keeping a patient mobile and toward this end the general concept of providing mobile traction has been previously considered. To the extent such prior art devices are known, the same do not provide for a high degree of mobility in that they are bulky and complicated in nature. Additionally the prior devices do not provide a high degree of anatomical control to the surgeon and hence do not provide for precise bone segment movement in all planes during reduction. Further, at least some of the prior art devices do not allow for rotation of the fracture ends and require lengthy assembly procedures on the operating table.

SUMMARY OF THE INVENTION

The present invention is embodied in an apparatus for application to a limb having a bone fracture for the positioning and subsequent retention of the fragment ends during mending while permitting the limb to be mobile.

The apparatus is embodied in what may be termed upper and lower pin holder assemblies in spaced relationship on the limb. Each assembly serves to receive a bone penetrating pin or pins with the pin ends being secured within the respective holder assembly. Accordingly, each holder assembly is securely affixed by a pin or pins to the distal end of a bone fragment.

Interconnecting the pin holder assemblies are circumferentially spaced elongate connector assemblies which adjustably couple the pin holder assemblies to one another to provide the surgeon a high degree of control over the bone ends during reduction. Said connector assemblies include spherical components enabling universal movement of the pin holder assemblies within a suitable range.

Important objectives of the present orthopedic apparatus include: the provision of an apparatus for use by surgeons in the reduction of a fracture which apparatus remains in place on the limb enabling the wearer to remain mobile; the provision of an apparatus utilizing pin holder assemblies each of which receive one or more pins to secure the bone fragment in place; the provision of an apparatus wherein bone penetrating pins are secured in a novel manner to their respective pin holder assemblies; the provision of an orthopedic apparatus which when in place leaves adequate clearance from the patient's skin to enable normal ventilation and care; the provision of an apparatus readily applied to the limb by reason of pivoting ring segments; the provision of an apparatus having a large proportion of reusable components to conserve patient expenses; the provision of an orthopedic apparatus including pin holder assemblies spaced apart along the injured limb and interconnected in a manner permitting a wide range of movements for a high degree of anatomical control; the provision of an orthopedic apparatus providing for the reception of a variable number of bone penetrating pins; the provision of an orthopedic device utilizing novel spherical coupling elements to interconnect the two pin holder assemblies in a universally adjustable manner; the provision of an orthopedic apparatus enabling distraction, impaction, rotation, angulation and offset of the distal ends of the bone fragments.

These and other objects of the invention will become subsequently apparent upon a reading and understanding of the following description.

BRIEF DESCRIPTION OF THE DRAWINGS

In the accompanying drawings:

FIG. 1 is a front elevational view of the present apparatus in place on a human lower leg shown in phantom lines;

FIG. 2 is a side elevational view of FIG. 1;

FIG. 3 is a horizontal sectional view taken downwardly approximately along line 3—3 of FIG. 1;

FIG. 4 is a view similar to FIG. 3 but taken approximately along line 4—4 of FIG. 1;

FIG. 5 is a sectional, elevational view taken approximately along line 5—5 of FIG. 3 and showing details of an expansible coupling;

FIG. 6 is a view similar to FIG. 5 with the coupling component expanded into locked engagement with a ring component of the pin holder assembly;

FIG. 7 is a plan view of an expansible coupling component removed from associated structure;

FIG. 8 is a front elevational view of FIG. 7;

FIG. 9 is a side elevational view of a surgical pin used in securing a pin holder assembly to a fractured bone;

FIG. 10 is a side elevational view of the pin shown in FIG. 9 inserted within a bone with the pin ends adapted to receive threaded fasteners shown backed off from the pin ends and from supporting wall fragments;

FIG. 11 is a side elevational view of a pin end inserted in support engagement with a wall fragment;

FIG. 12 is a side elevational view of a pin end and modified threaded fastener;

FIG. 13 is a side elevational view of an alignment bow for pin guidance;

FIG. 14 is a front elevational view of a modified expansible spherical coupling component removed from associated structure;

FIG. 15 is a fragmentary elevational view of a solid wall structure with pin ends embedded therein;

FIG. 16 is an end elevational view of a fastener for a surgical pin;

FIG. 18 is a view similar to FIG. 1 but showing a modified form of the invention;

FIGS. 19 and 20 are plan views taken along lines 19—19 and 20—20 of FIG. 18;

FIG. 21 is an enlarged detail view of a modified connector assembly taken along line 21—21 of FIG. 18;

FIG. 22 is a fitting for wall insertion which receives and locks the end of a surgical pin.

DETAILED DESCRIPTION OF THE PREFERRED EMBODIMENTS

Figure 17:
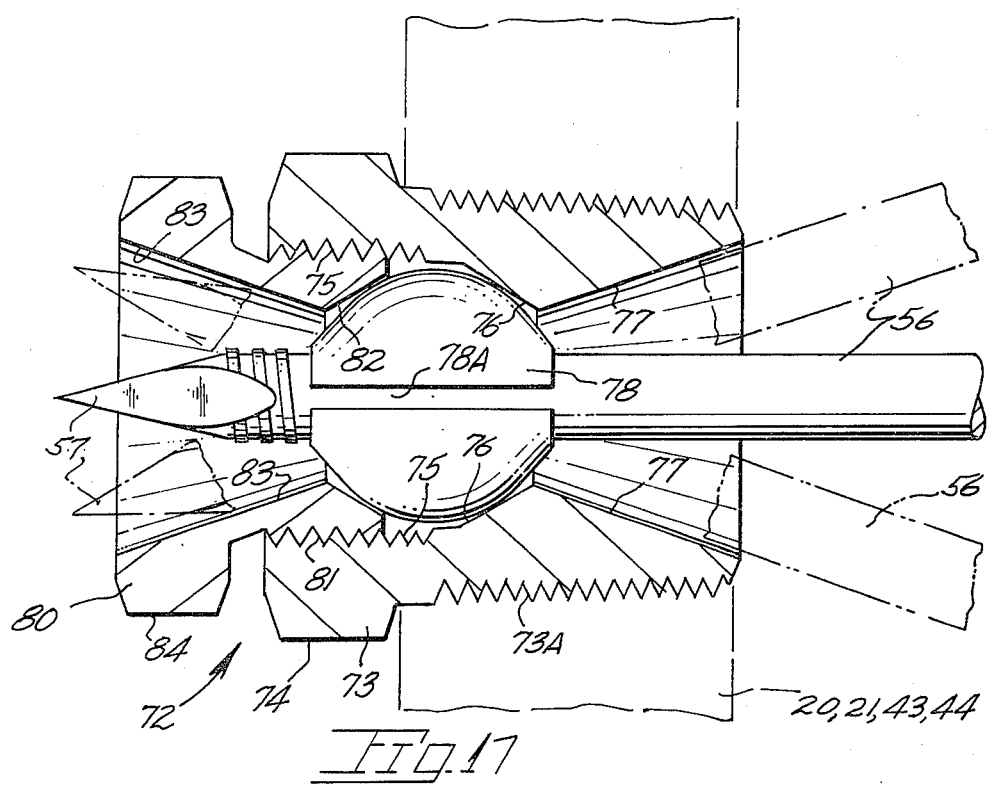
FIG. 17 is a side elevational view of a modified pin fastener arrangement.

With continuing reference to the accompanying drawings wherein like reference numerals indicate parts similarly identified in the following description, the reference numerals 1 and 2 indicate generally first and second pin holder assemblies which in the present disclosure may properly be preferred to as upper and lower assemblies for the sake of convenience. While said pin holder assemblies are shown in FIGS. 1 and 2 applied to the lower leg L of a patient it is to be understood that the present apparatus is equally suited with minor size modification to any limb, human or lower animal.

With attention to FIGS. 1, 2 and 3 wherein upper pin holder assembly 1 is disclosed, the reference numeral 3 indicates a closed circular ring structure comprising a front ring segment 4 and a rear ring segment 5. Reduced ends at 4A and 5A of the ring segments each receive a fastener 6 extending therethrough and in threaded engagement with reduced ends 4A. Countersunk fastener heads and oversize bores in reduced ends 5A permit one of the fasteners 6 to serve as a pivot for the ring segments upon removal of the remaining fastener to permit opening and closing of the ring structure about a limb.

Front and rear ring segments 4 and 5 define arcuately extending openings 7, 8 and 9 formed about the segment's center. As best viewed in FIGS. 3, 5 and 6, opening 7 is defined by concave wall surfaces 10 and 11, the latter surface being on a curved plate 12 secured to front ring 4 by segment fasteners 13. Rear ring segment openings at 8 and 9 are of somewhat greater length but similarly defined by concave opposed wall surfaces at 14 and 15 with surfaces 15 being on segmental clamping plates 16. Said segmental plates are secured by threaded fasteners 17.

For reception of later described bone penetrating pin means, I provide upstanding, curved wall structures at 20 and 21 each shouldered along its lower edge as at 20A–21A for rested engagement with front ring segment 4. Screws (not shown) secure the walls lower edges to the inner surface of front ring segment 4. The walls 20 and 21 are preferably of a synthetic resinous material for the reception of later described fasteners.

The upper edges of walls 20 and 21 are also shouldered 20B–21B for secured attachment to a semicircular bridge 23. The walls 20, 21, front ring segment 4 and semicircular bridge 23 are joined in a permanent, rigid manner. Loads imparted to the walls, as hereinafter described, are transmitted to front ring segment 4 without wall deflection.

With further regard to walls 20 and 21, the same are provided with rows of axially spaced, aligned apertures at 24 and 25 for the reception of inserted surgical pin means. The apertures 24 and 25 may be of truncated conical shape tapering slightly in an inward direction. As viewed in FIG. 3 the openings 24–25 are in axial alignment with the axis intersecting the major axis of a broken bone B. A wide selection of pin locations are hence provided to suit specific fracture characteristics. A modified wall structure comprehends a solid wall, as later described, for reception of an embedded pin end.

Lower pin holder assembly 2 is very similar to the upper pin holder assembly just described but preferably is of somewhat lesser cross section and of a tapered nature for the sake of patient convenience. Reference numeral 26 indicates a closed circular ring structure of the lower pin holder assembly comprising a front ring segment 27 and a rear ring segment 28. The segment ends are reduced at 27A and 28A to permit overlapping of same and the common reception of fasteners 30. Said fasteners terminate in threaded securement with reduced segment ends 27A with the superjacent segment ends 28A having shomewhat oversize bores and countersunk to receive the heads of fasteners 20. A single fastener 30 may serve as a pivot during opening and closing movement of ring structure 26 about a limb.

Front and rear ring segments are at 27 and 28 each defining arcuately extending concentric openings at 33, 34 and 35. The openings 33–35 are defined by concave wall surfaces such as those earlier described in conjunction with upper pin holder assembly 1 and as typically shown in FIGS. 5 and 6. A curved plate 36 is secured to front ring segment 27 by fasteners 37. Rear ring segment 28 defines openings 34 and 35 in conjunction with curved plates 40 and 41 held in place by fasteners 42. The openings in ring structure 26 are all defined by concave wall surfaces to receive spherical components of later described connector assemblies which join the upper and lower pin holder assemblies.

In place on lower circular ring structure 26, for the reception bone inserted pins, are depending walls 43 and 44 each shouldered along its upper edge as at 43A and 44A for seated engagement with ring structure 26 and specifically front ring segment 27 thereof. Said front ring is correspondingly adapted to assure retentive engagement of the wall with countersunk fasteners completing the securement.

The lower edges of walls 43 and 44 are also shouldered at 43B and 44B for secured attachment to a semicircular bridge 49. Accordingly, walls 43, 44, front ring segment 27 and semicircular bridge 45 are joined in a rigid, permanent manner wherein loads imparted to the walls 43 and 44 by later described pins are bourne without wall of deflecton.

In continuing similarity to upper pin holder assembly 1, the walls 43, 44 are provided with rows of aligned apertures 45 and 46 for passage and retention of surgical pin means. The wall openings, as before, are preferably of truncated cone shape with an inwardly directed taper with the openings in one wall being in axial alignment with a corresponding opening in the remaining wall with a selected aperture axis intersecting the axis of a distal bone fragment. As before, one of said walls may be solid (FIGS. 11 and 15) to receive the embedded end of a surgical pin.

Connector assemblies are embodied in shafts 47 each adjustably coupled, as later described, to the upper and lower pin holder assemblies to permit a wide range of movement of one or both of said assemblies during fracture reduction. Spherical coupling components are indicated at 50 and, as best shown in FIGS. 7 and 8, are essentially of ball shape and expansible by reason of being bifurcated. Retainers at 51 engage anti-rotation appendages 52 on the coupling components with end segments engaging said appendages enabling outward displacement of the coupling halves as seen in FIG. 6. Expanding of the coupling is accomplished by conical bodies 53 formed on adjustable nut elements 54. The truncated ends of said projections move within a corresponding conical recess defined by a spherical coupling component to bias the halves thereof into biased engagement with the concave wall surfaces of their respective ring segments. In FIG. 14 I show a modified spherical coupling component 50' similar to the above described but having a circular retainer ring at 48 within semicircular grooves of each half. A bridge at 50A prevents ring rotation while appendages 52' prevent component rotation. The shafts 47 are threaded to receive adjustable elements 54 with opposite rotation of the adjustable nut elements associated with one spherical component of one coupling arrangement causing closing movement between two nut elements and hence expansion of the spherical component while like rotation of said elements of one coupling results in axial repositioning of the spherical component along shaft 47. Such axial movement imparts movement to the associated circular ring structure 3 or 26. For example, such advancement of all six nut elements associated with upper ring structure 3 will impart movement to same repositioning same towards or away from the remaining ring structure. Such positioning of a pair of nut elements 54 along a shaft 47 will tend to move a ring structure out of parallel relationship with the remaining ring structure which is of importance in achieving alignment of the fracture ends to overcome undesired angulation complications.

Adjustment of nut elements 54 and hence coupling components 50 enables the surgeon to accomplish the necessary bone movements of distraction, impaction, rotation (manually), angulation and offset. The movement of the ring structures 3 and 26 are all made in incremental fashion and may be made with the aid of fluoroscopy. The coupling components, by reason of their universal movement capability, permit the upper and lower ring structures 3 and 26 to be shifted manually out of axial alignment and subsequently locked into an offset relationship thereby providing a capability for correcting offset problems of the fracture ends.

With attention now to FIGS. 9 and 10 wherein surgical pin means are disclosed, a pin 56 is conventionally provided with a cutting end or tip 57 which pin is partially threaded for bone penetration. Pin fasteners 58, shown in FIG. 10, are of the collet type slotted in a lengthwise direction at 59. The pin means includes a flat sided end segment 56A suitable for engagement with a power drill chuck at C. An annular fracture groove at 56B permits snapping off of end segment 56A upon the pin being inserted into place and secured to a wall structure by means of fasteners 58. Said fasteners are externally threaded and of an outer diameter at their smaller ends to facilitate starting and subsequent threaded engagement with a wall opening 24-25, 45-46. Additionally the fasteners 58 define internal bores at 58A for passage of the pin ends during seating of the fasteners. Flats at 60 on the fasteners permit the use of a wrench to firmly seat the threaded fastener into pin retentive engagement with a wall opening to assure locking in place of the pin end. The leading end of each fastener is divided into quadrants each having a self tapping edge as at 61.

With attention to FIG. 15, a fragment 62 of a solid wall is shown which well may be used in pin supporting cooperation with an apertured wall of the type earlier described. In the instance of a solid wall, the pin tip 57 seats within the wall material which, as aforesaid, is of a strong resinous material capable of retaining the pin end against accidental displacement.

In FIG. 12, a modified fastener 63 is disclosed intended for use in the case of a pin 56 being inserted into place along an axis other than the common axis of two aligned wall openings. Fastener 63 is similar to earlier described fastener 58 in that tool receiving flats are provided at 64. External threads at 65 engage and seat the fastener within a wall opening. For retention of the offset pin tip 57, a body 66 of resinous material is mounted on the leading end of the metallic portion of the fastener as by a stud at 67. Advancement of fastener 63 urges resinous body 66 into tip securing engagement.

In FIG. 13, an alignment aid 69 is shown which is of bow configuration having enlarged ends 70 each of which is of conical shape and slotted in a radial direction to permit central reception of a surgical pin 56 for subsequent guidance of same along the aligned axes of two aligned wall openings. Upon passage of the pin tip 57 through the bone and into the proximity of the other wall aperture, the bow is removed to disengage the enlarged ends 70 from the aligned wall apertures whereupon the slots in said enlarged ends permit radial disengagement from the pin.

In use, the apparatus is designed to come pre-assembled and pre-adjusted by the nursing staff and to be placed on the patient in the operating room under suitable anesthesia. By removing single fasteners at 6 and 30 the ring structures may be hinged open for limb application. Prior to placing the device upon the patient the length of the patient's leg is ascertained. By adjustment of nut elements 54 on shafts 47 the spacing of the ring structures 3 and 26 can be pre-set and locked into position.

With the device hinged open in the operating room the leg is placed into position within the circular ring structures and is held in its approximate reduced position. Pins 56 are then inserted through proper holes in the upright walls. The leg and the device are manipulated in order to provide clearance between the soft tissues of the leg and the apparatus. Similarly this step is performed on the leg below the fracture site. Several pins 56 may be placed, but generally speaking, two or three are adequate. The apertures in the upstanding walls should be so selected to provide for aligned placement of the pin as is reasonably possible. Once the pins are placed and properly secured into the walls, a self-tapping fastener 58 is secured in place over each end. A wrench tool is applied to each fastener 58 whereby same will cut and tap its own thread ultimately locking itself into place in the wall aperture.

The tapered wall holes start with an outside diameter of 9/16 of an inch and terminate with an inside diameter of ¼ inch. The suggested width of the plastic wall is approximately ½ inch. Following proper seating of the pins, excess lengths on either side may be cut off or bent over to avoid protruding points.

Now that the unit is firmly seated on the leg above and below the fracture site any manipulations of the leg may now take place through loosening and adjusting of nut elements 54. Distraction of the fracture site may be accomplished by loosening the outside nut elements 54 on shafts 47 in all three locations on the lower or upper pin holder assemblies. The inside bolts are then advanced.

Impaction of the fragment may be obtained by moving the inside nut elements 54 toward the center of shaft 47 and advancing the outside nut elements in the same direction. Again, this function is performed on only one ring at a time to maintain longitudinal alignment. If angulation is required such is accomplished by non-uniform extension or retraction of the nut elements 54 of the connector assemblies. Angulation in any plane may be obtained by loosening all connector assemblies around the arcs of each ring structure and retightening same after fracture repositioning.

If it is necessary to offset the fracture ends all nut elements 54 must be loosened, the fracture aligned and all nut elements tightened. If it is necessary to rotate a bone fragment around an axis with respect to the remaining bone fragment, the nut elements 54 may be released on all three positions of one pin holder assembly and the ring rotated within the limits of the slots shown. If more rotation is required, the same steps may be performed on the remaining pin holder assembly. This device accordingly provides a highly adaptable apparatus for angulation in any plane, offsetting in any plane, distraction, impaction and rotation of the fracture.

The patient may have additional connector assemblies added to the device for increased longitudinal strength. Additional pins 56 may be added for additional support, if necessary. The apparatus is compact and since it is largely constructed of aluminum with much open space, it is very light with many of the parts being reusable.

In instances where a limb has more than one fracture site, the semicircular bridges at 23 and 49 may be removed and a ring structure similar to those at 3 and 26 applied to the distal edges of the upright walls. The added ring structures serve to receive the ends of additional connectors which in turn may secure in place still other pin holder assemblies of the type above described. Accordingly, an entire limb may be reduced while permitting the patient to remain mobile.

In FIG. 17 a modified pin fastener arrangement is disclosed. A fastener assembly is indicated generally at 72 and provides for locking a surgical pin end to an apertured wall structure 20, 21, 43, 44 throughout a range of pin to wall relationships per the extreme broken line pin positions of FIG. 17. The assembly includes a wall engaging socket member at 73 externally threaded at 73A for wall engagement. Said socket member is provided with tool receiving flats at 74 and is of open construction having internal threads 75 merging inwardly with a conical wall 76. The pin receiving end of socket 73 is provided with an interior conical wall 77 which provides an enlarged opening to accommodate entry of a misaligned pin. Disposed within socket member 73 is a movable collet 78 of spherical configuration, slotted at 78A to permit collet closure about surgical pin 56. Acting on said collet is compression element 80 threaded at 81 with a conical compression wall at 82. Wall 82 and socket wall 76 cooperate upon advancement of compression element 80 to close collet 78 about pin 56. For purposes of accommodating a range of pin to fastener relationships, compression element also includes a conical wall surface 83. A tool applied to the flats 84 of compression element 80 enables locking of the pin to fastener 83 regardless of the pin and fastener being other than coaxial. Conical walls 77 and 83 define tapers of approximately 37° degrees.

With attention now to the form of the invention disclosed in FIGS. 18 through 22, first and second pin holder assemblies are indicated generally at 91 and 92. Said assemblies may be of composite or cast construction with said first pin holder assembly having front and rear segments 93 and 94 joined by a pivot pin 95 and a lock 96 which enables opening of the assembly for placement about an injured limb. Said second pin holder assembly is similar, with front and rear segments 97, 98 joined by a pivot pin 100 and a lock 101.

Wall structures at 102 are flanged at 102A for mounting in recesses as at 97A in each pin holder assembly with set screws 104 securing same in place. Each of said wall structures is of a high density, synthetic material and defines apertures 105 for the reception of surgical pin securing means. Both full and half surgical pins may be supported by surgical pin fastener assemblies earlier described, or by a later described fitting. Additional pin holder assemblies may be attached to the wall structures shown to enable immobilizing the full or major portion of an injured limb.

In FIGS. 18 through 21 I shown modified connector assemblies each including a shaft 107 with upper and lower threaded segments on which are carried adjustable and lockable nut elements 108 having conical ends for abutment with a sleeve of a ball and sleeve component at 110. A ball component 110A thereof is preferably of a durable synthetic material and in internal fixed engagement with the irregular, knurled surface of a sleeve component 110B. A clamping member 111 is adjustably affixed to a pin holder assembly segment by cap screws 112 to permit frictional engagement of said member in a universal manner with ball component 110A and subsequent locking of same after reduction of the fracture. Sleeve component 110B and hence adjustment of a pin holder assembly relative to a remaining like assembly is accomplished by the advancement of nut elements 108 along shaft 107 and subsequent biasing of same against slidable sleeve 110B.

Pin means of the modified form may be as described in conjuncion with the first form of the invention. A modified fitting for securement of a surgical pin end is shown in FIG. 22. The fitting 113 is of a tapered, threaded design for threaded insertion within an aperture 105 in one of the wall structures 102 with tool receiving flats thereon at 113A. The inner end of the fitting is conical at 114 to displace an advancing surgical pin end towards a central bore 115 in the fitting. A set screw 116 is provided to firmly seat and lock the inserted end of a surgical pin in place within the fitting.

The present apparatus may be utilized in the treatment of burn victims as it permits a high degree of access to the limb exterior. The apparatus may also serve to immobilize an elbow or knee and to retain same against retraction during treatment of the arm or leg.

While I have shown but a few embodiments of the invention it will be apparent to those skilled in the art that the invention may be embodied still otherwise without departing from the spirit and scope of the invention as claimed.

Having thus described the invention what is desired and claimed to be secured under a Letters Patent is:

1. An orthopedic apparatus for the reduction and immobilizing of the distal end segments of a fractured bone, said apparatus comprising,
   first and second pin holder assemblies each including pairs of pin receiving apertured wall structures, said assemblies adapted for disposition about a limb above and below the fracture site,
   pin means adapted for penetration of the bone segments and supported by at least one of the wall structures of said pair of wall structures of the first and second pin holder assemblies, and
   elongate connector assemblies coupling said pin holder assemblies in adjustable spaced relationship, said connector assemblies each including a threaded shaft, pairs of axially adjustable elements thereon, ball and sleeve components disposed intermediate each of said pair of elements, clamping members carried by and spaced about on each of said pin holder assemblies for universal adjustable and clamping engagement with said ball and sleeve components, said axially adjustable elements operable upon axial repositioning to move a ball and sleeve component and thereby enable incremental varying of the spaced relationship between said pin holder assemblies, momentary release of said clamping members permitting alignment of the fracture ends by manual positioning of said pin holder assemblies, said axially adjustable elements thereafter adapted for advancement of a pin holder assembly and subsequent locked engagement with an intermediate ball and sleeve component for retention of the fracture ends in compression.

2. The orthopedic apparatus claimed in claim 1 wherein said pin holder assemblies each comprise a closed ring structure, said closed ring structures each defining a pair of recesses for the inserted installation of said wall structures.

3. The orthopedic apparatus claimed in claim 2 wherein said ring structures additionally define recesses on their upper and lower surfaces to permit the installation of said wall structures on both upper and lower sides of a ring structure.

4. The orthopedic apparatus claimed in claim 1 wherein said sleeve has an irregular surface thereon to assure ball and sleeve integrity.

5. The orthopedic apparatus claimed in claim 1 wherein said pin means includes a surgical pin fastener assembly insertable within one of said wall apertures and securing the pin end to the wall structure, said fastener assembly including a socket member, pin engaging collet means within said socket member, a compression member carried by said socket member and adapted for biasing engagement with said collet means to lockably engage the latter with said surgical pin.

6. The orthopedic apparatus claimed in claim 5 wherein said socket member and said compression member define conical openings of a size to admit entry of a surgical pin having an axis offset to the major axis of said fastener assembly.

7. The orthopedic apparatus claimed in claim 6 wherein said collet means is of spherical configuration.

8. The orthopedic apparatus claimed in claim 1 wherein said pin means includes a surgical pin fastener assembly including a threaded fitting for installation within a wall aperture, said fitting defining a central bore and having a conical wall at its inwardly disposed end for the reception and guidance of a surgical pin end, said fitting additionally including a set screw for locking engagement with the surgical pin.

9. The orthopedic apparatus claimed in claim 1 wherein said pin means includes a surgical pin, an externally threaded pin fastener defining an internal bore for reception of a pin end segment, said fastener having tool receiving surfaces thereon and being of the collet type slotted in a lengthwise direction and adapted for frictional engagement with a pin end segment upon advancement of said fastener into an aperture in one of said wall structures.

10. The orthopedic apparatus claimed in claim 1 additionally including an alignment aid of bow configuration having ends adapted for temporary engagement with aligned apertures in the wall structures of a pin holder assembly, said ends axially guiding s surgical pin being installed.

* * * * *